US011034093B2

United States Patent
Cound et al.

(10) Patent No.: US 11,034,093 B2
(45) Date of Patent: Jun. 15, 2021

(54) APPLICATOR MITT ASSEMBLY SYSTEM

(71) Applicant: SLG Brands Limited, Gloucester (GB)

(72) Inventors: Tim Cound, Gloucester (GB); Jeremy Jones, Hereford (GB); John Teece, Herefordshire (GB)

(73) Assignee: SLG BRANDS LIMITED, Cheltenham (GB)

( * ) Notice: Subject to any disclaimer, the term of this patent is extended or adjusted under 35 U.S.C. 154(b) by 0 days.

(21) Appl. No.: 16/235,279

(22) Filed: Dec. 28, 2018

(65) Prior Publication Data

US 2019/0134917 A1 May 9, 2019

Related U.S. Application Data

(62) Division of application No. 15/455,715, filed on Mar. 10, 2017, now Pat. No. 10,201,934.

(30) Foreign Application Priority Data

Jul. 27, 2016 (GB) ..................................... 1612964

(51) Int. Cl.
*B29C 65/02* (2006.01)
*A41D 19/04* (2006.01)
(Continued)

(52) U.S. Cl.
CPC .............. *B29C 65/02* (2013.01); *A41D 19/01* (2013.01); *A41D 19/04* (2013.01); *A45D 34/04* (2013.01);
(Continued)

(58) Field of Classification Search
None
See application file for complete search history.

(56) References Cited

U.S. PATENT DOCUMENTS 2,040,052 A * 5/1936 Lammott ............... A41D 19/02
2/169
3,717,538 A 2/1973 Hartung
(Continued)

FOREIGN PATENT DOCUMENTS

DE 252795 A1 12/1987
DE 29604143 U1 8/1996
(Continued)

OTHER PUBLICATIONS

Machine translation of abstract and paragraph 2 of p. 3 of foreign patent document DD252795A1. Dec. 30, 1987.
(Continued)

*Primary Examiner* — Chinessa T. Golden
(74) *Attorney, Agent, or Firm* — Ashley Law Firm P.C.; Stephen S. Ashley, Jr.

(57) ABSTRACT

An applicator mitt assembly system comprises an applicator mitt tooling including: a tooling body having a mitt-perimeter cutter and weld bead thereon which are shaped to a perimeter of a mitt to be cut; a heating element associated with the tooling body which is shaped so as to substantially match a shape of the weld bead to create a perimeter weld for the mitt when engaged with the tooling body; and an ejector platen which is actuatable relative to the tooling body to eject a cut and welded mitt. A conveyor device is adapted to feed mitt material towards the tooling and a tooling actuator adapted to actuate the tooling relative to the conveyor device to allow the cutter to cut mitt material at the conveyor device. A discrete applicator mitt tooling, method of assembling an applicator mitt, and welded applicator mitt are also provided.

9 Claims, 5 Drawing Sheets

(51) Int. Cl.
| | |
|---|---|
| *B29C 65/18* | (2006.01) |
| *B29C 65/30* | (2006.01) |
| *B29C 65/74* | (2006.01) |
| *B29C 65/00* | (2006.01) |
| *B29D 99/00* | (2010.01) |
| *B29C 65/78* | (2006.01) |
| *A41D 19/01* | (2006.01) |
| *A45D 34/04* | (2006.01) |
| *A45D 40/26* | (2006.01) |
| *B29L 31/48* | (2006.01) |
| *A61M 35/00* | (2006.01) |
| *B29L 31/00* | (2006.01) |

(52) U.S. Cl.
CPC ............ *A45D 40/26* (2013.01); *B29C 65/18* (2013.01); *B29C 65/305* (2013.01); *B29C 65/7441* (2013.01); *B29C 65/7891* (2013.01); *B29C 66/005* (2013.01); *B29C 66/0062* (2013.01); *B29C 66/1122* (2013.01); *B29C 66/244* (2013.01); *B29C 66/43* (2013.01); *B29C 66/727* (2013.01); *B29C 66/729* (2013.01); *B29C 66/72343* (2013.01); *B29C 66/7392* (2013.01); *B29C 66/81419* (2013.01); *B29C 66/81427* (2013.01); *B29C 66/81821* (2013.01); *B29C 66/8322* (2013.01); *B29C 66/8432* (2013.01); *B29C 66/91212* (2013.01); *B29C 66/91231* (2013.01); *B29D 99/0067* (2013.01); *A61M 35/10* (2019.05); *B29C 65/787* (2013.01); *B29C 66/133* (2013.01); *B29C 66/81417* (2013.01); *B29C 66/863* (2013.01); *B29L 2031/4864* (2013.01); *B29L 2031/726* (2013.01); *Y10T 156/1054* (2015.01)

(56) References Cited

U.S. PATENT DOCUMENTS

| | | | |
|---|---|---|---|
| 3,975,885 A | | 8/1976 | Carlisle |
| 4,999,081 A | | 3/1991 | Buchanan |
| 6,770,581 B1 | * | 8/2004 | DeMott ................ A47G 23/03 428/91 |
| 2005/0102786 A1 | * | 5/2005 | Dunkley ................ A45D 34/04 15/227 |
| 2007/0048062 A1 | * | 3/2007 | Brunner ................ A47L 13/19 401/7 |
| 2009/0094722 A1 | * | 4/2009 | Alden ............... A41D 19/01529 2/20 |

FOREIGN PATENT DOCUMENTS

| | | |
|---|---|---|
| EP | 0583893 A1 | 2/1994 |
| FR | 2902338 A1 | 12/2007 |
| GB | 1527932 A | 10/1978 |
| GB | 2407025 A | 4/2005 |
| JP | S5743824 A | 3/1982 |
| KR | 20110125528 | 11/2011 |
| KR | 101161334 B1 | 7/2012 |
| WO | WO03016029 A2 | 2/2003 |
| WO | WO2013064924 A1 | 5/2013 |

OTHER PUBLICATIONS espace.net. Translation of foreign patent document DE29604143U1. Aug. 22, 1996.
Machine translation of abstract of foreign patent document FR2902338A1. Dec. 21, 2007.
Machine translation of foreign patent document JPS5743824A. Mar. 12, 1982.
European Patent Office. European Search Report for European Patent Application No. EP17177522, dated Dec. 6, 2017.
UK Intellectual Property Office, Search Report for Patent Application No. GB1612964.5, dated Aug. 11, 2016.
UK Intellectual Property Office, Examination Report for Patent Application No. GB1612964.5, dated Nov. 30, 2016.
Machine translation of specification of foreign patent document FR2902338A1. Jul. 6, 2018.
English translation of foreign patent document KR101161334B1. Aug. 2, 2019.
European Patent Office. Examination Report for European Patent Application No. 17177522.4, dated Jun. 12, 2019.
European Patent Office. Examination Report for European Patent Application No. 17177522.4, dated Dec. 8, 2019.

\* cited by examiner

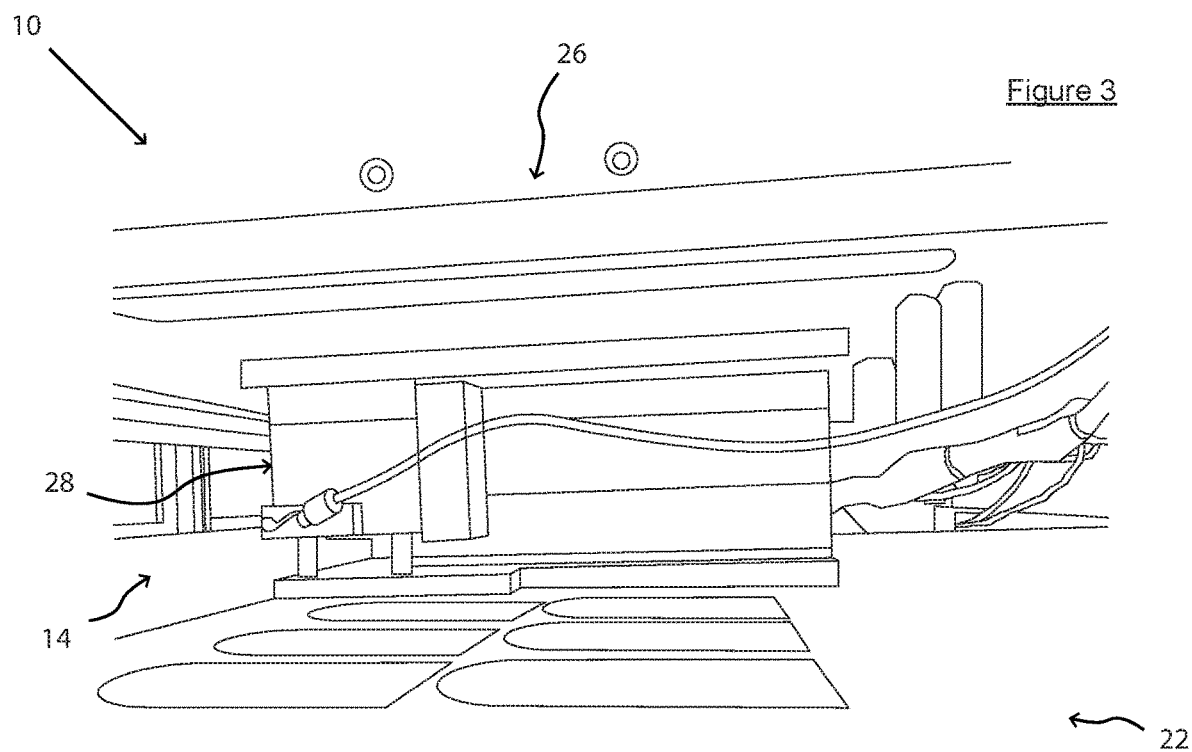

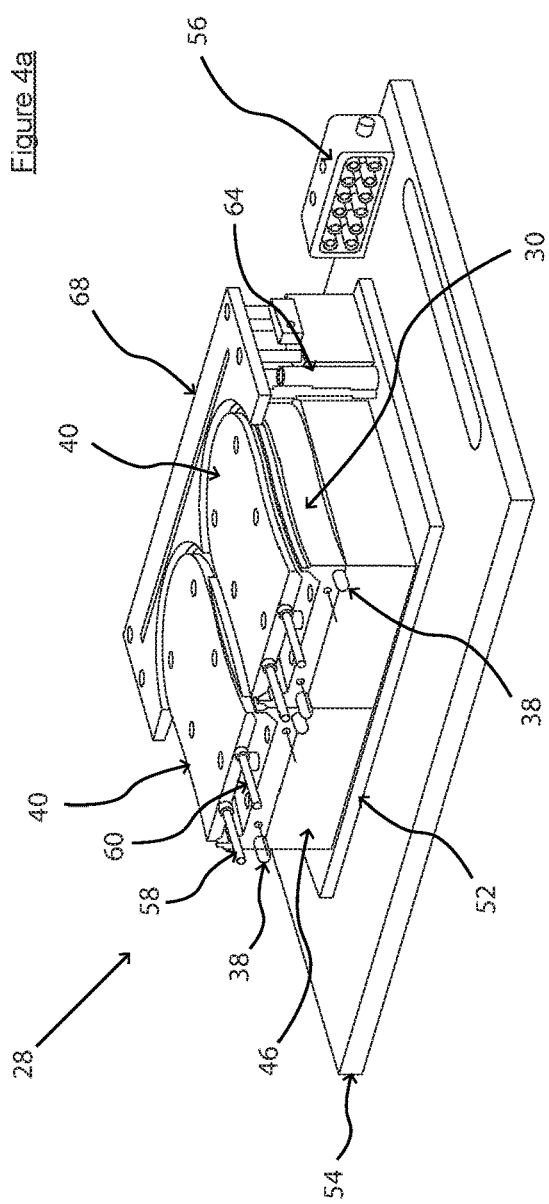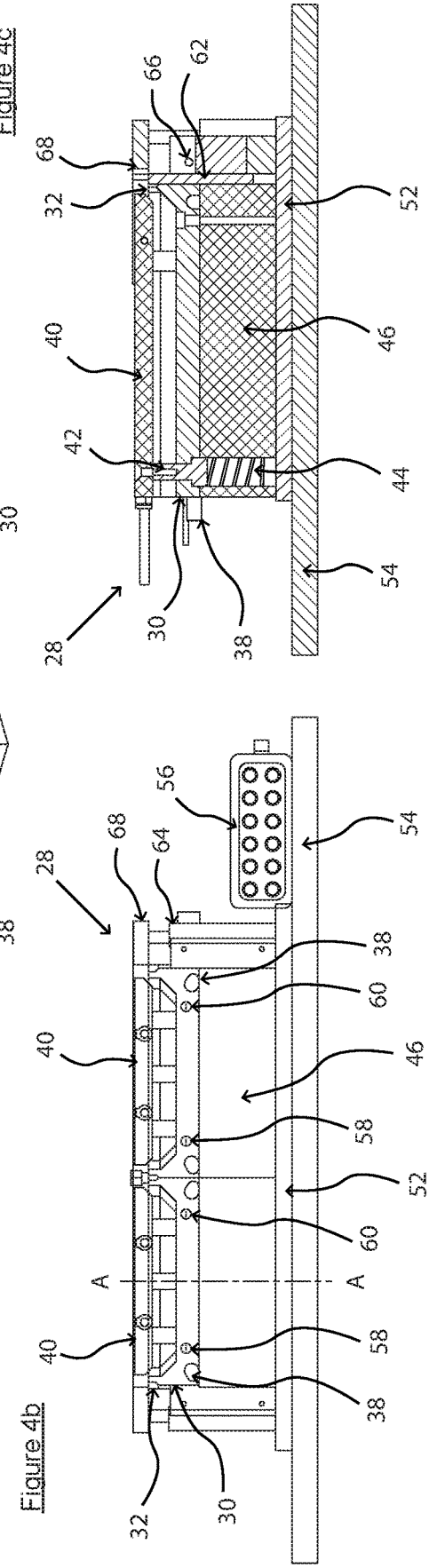

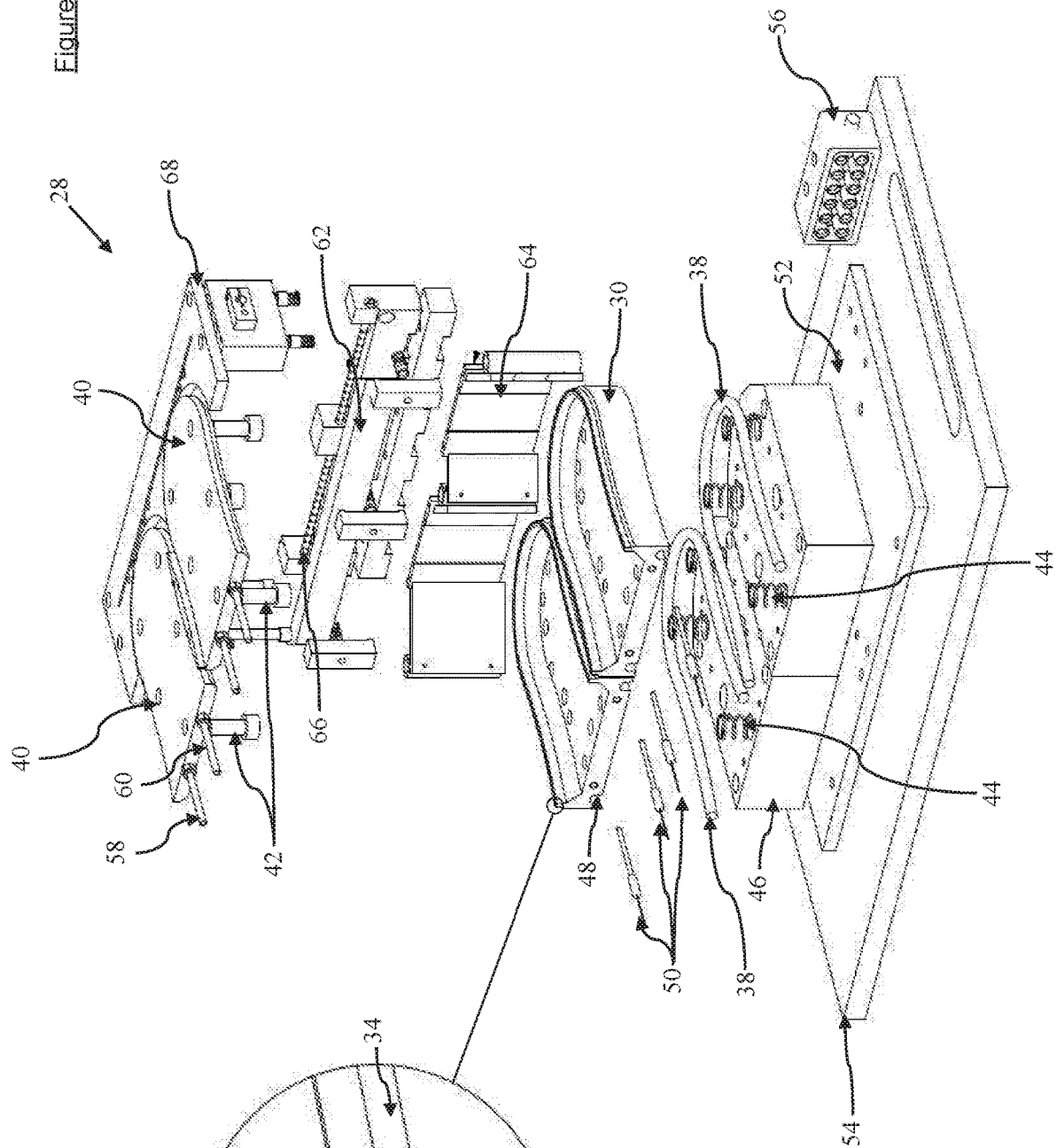
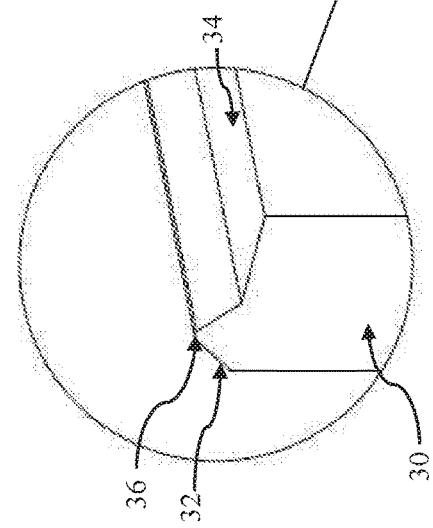
Figure 4d
Figure 4e

APPLICATOR MITT ASSEMBLY SYSTEM

CROSS REFERENCE TO RELATED APPLICATIONS

This application is a divisional application of U.S. patent application Ser. No. 15/455,715, filed Mar. 10, 2017, which claims priority to British Patent Application No. 1612964.5, filed Jul. 27, 2016. All of said applications are incorporated herein by reference.

TECHNICAL FIELD OF INVENTION

The present invention relates to an applicator mitt assembly system for the manufacture of applicator mitts particularly for the application of creams, lotions, foam mousses or sprays, such as tanning lotion. The invention also relates to an applicator mitt tooling for use in the system, a method of assembling an applicator mitt, and to an applicator mitt formed via the method.

BACKGROUND OF INVENTION

An applicator mitt is a glove-like item which has at least one surface which is suitable for the application of a tanning lotion to the body of a user, for instance, the surface typically being formed from a foam or spongiform material. Such applicator mitts are most commonly used in the application of tanning lotion.

The applicator mitt must fulfil several requirements: firstly, the applicator surface of the mitt must be suitable for retaining and applying a liquid or colloidal substance to the body of a user, and therefore must generally be porous; secondly, the applied substance must not leach through the applicator surface so as to contact the user's hand, and there must therefore be some form of barrier between the applicator surface and the interior of the applicator mitt; finally, the opening of the applicator mitt must be suitable for receiving a user's hand, which means that a side of the applicator mitt which is opposite to the applicator surface must be adequately secured to the applicator material.

Additionally, applicator mitts should be machine-washable, preferably up to 40° C. in order to adequately cope with the staining associated with tanning products, should have a strong and consistent seam to avoid breakage during use, and should be aesthetically pleasing. An applicator mitt should also feel soft and comfortable against the user's skin.

Applicator mitts have therefore traditionally been constructed by cutting the respective materials to size, which will be a laminated foam or sponge for the applicator side of the applicator mitt, and a fabric material for the other side. Following cutting, the two materials are sewn together, bar-tacked together for security, and then trimmed to size. This is a labour-intensive procedure. The increase in demand for applicator mitts has therefore not been adequately supported by the manufacturing ability to produce high volumes of applicator mitts.

The present invention seeks to provide a mechanism by which large volumes of high-quality, strong and sturdy applicator mitts can be produced.

SUMMARY OF THE INVENTION

According to a first embodiment of the invention, there is provided an applicator mitt assembly system comprising an applicator mitt tooling including a tooling body having a mitt-perimeter cutter and weld bead thereon which are shaped to a perimeter of a mitt to be cut and welded, the mitt-perimeter cutter projecting above the weld bead in a direction away from a base of the tooling body; a heating element associated with the tooling body, the heating element being shaped so as to match a shape of the weld bead so as to create a perimeter weld for the mitt when the mitt contacts the weld bead; and an ejector platen which is actuatable relative to the tooling body to eject a cut and welded mitt away from the tooling body, the ejector platen being thermally decoupled from the tooling body; a conveyor device adapted to feed uncut and unwelded mitt material towards the applicator mitt tooling; and a tooling actuator adapted to actuate the applicator mitt tooling relative to the conveyor device to allow the mitt-perimeter cutter to cut the uncut and unwelded mitt material at the conveyor device.

The provision of a system for manufacturing applicator mitts on an industrial scale allows for the efficient creation of applicator mitts having a strong and secure seam which, in this case, may be a heat-welded join. One of the problems of welding fabric and foam materials to one another has been in avoiding the welding of the layers together across the entire span of the applicator mitt. The shaping of the heating element circumvents this issue; welding only occurs at or adjacent to the mitt-perimeter cutter. Furthermore, the proximity of the mitt-perimeter cutter and the heating element eliminates the traditional excess material overhang which can be formed. Such an overhang, in which the welded join extends outwardly of the desired perimeter of the applicator mitt appears unsightly and can be scratchy to a user's body during application of the lotion or cream. An embodiment of the present invention neatly forms the weld bead simultaneously with the cutting of the mitt material, eliminating or limiting the potential for the formation of overhanging material to be present. Furthermore, the ejector platen acts as a thermal barrier to prevent the interior of the applicator mitt material from becoming welded whilst the perimeter is welded. This also minimises the material wastage in the manufacture of the applicator mitts.

The applicator mitt tooling can further comprise a mitt-opening cutter. The mitt-opening cutter is thermally insulated from the heating element, and/or may be offset relative to the mitt-perimeter cutter on the applicator mitt tooling. There may also be provided a mitt-opening-cutter web ejector to prevent the cutter from sticking to the applicator mitt and/or web of material to be cut.

The opening of the applicator mitt must be provided such that a user can insert their hand. One of the obstacles overcome in the present invention is how to avoid accidental welding of the opening during the heating process. The provision of a dedicated mitt-opening cutter which can be thermally isolated and/or spaced apart from the heating element and main mitt-perimeter cutter can help to overcome this problem.

Optionally, the mitt-perimeter cutter may be formed having a bevelled cutting edge and additionally or alternatively may project from the weld bead by no more than 3 mm, preferably by no more than 1 mm, and most preferably no more than 0.5 mm.

The shaping of the mitt-perimeter cutter can be optimised so as to create a neat edge of the final applicator mitt, such that there is a smooth edge, gradient or curvature at or adjacent to the welded join. This creates smooth applicator surfaces, whilst also being more visually appealing to a user, and less likely to scratch a user during application of the tanning solution.

The applicator mitt assembly system may include a heatsink at or adjacent to the heating element. Said heatsink may be connected to the tooling body, the heating element being positioned in a recessed portion of the tooling body which is adjacent to the heatsink.

The provision of a heatsink engaged with the tooling body provides a reservoir of thermal energy adjacent to the heating element. This mitigates the effect of air cooling on the applicator mitt tooling as it is actuated within the applicator mitt assembly system. This leads to a more energy efficient system, whilst also decreasing the time required for the heating element to attain a sufficient welding temperature between subsequent cuts and welds of the mitt material.

Preferably, the heating element may be elongate, in which case, the heating element may be or substantially be U-shaped or tulip-shaped. The heating element may additionally or alternatively be contoured or curved to a profile of applicator mitt to be welded.

A glove-like applicator mitt is the most useful type of product for the application of tanning lotion, and a U-shaped or tulip-shaped mitt having a waisted portion may advantageously fit a user's hand most effectively. Contoured or curved applicator mitts also may have a more appealing aesthetic than those with straight-edged sides, which can be challenging to form using traditional techniques.

The ejector platen may optionally include a fluid coolant inlet and outlet to permit fluid cooling thereof. Furthermore, the ejector platen may also include a plurality of sprung ejector pins to permit actuation relative to the tooling body.

During the development of the present invention, it was found that there was a tendency for the ejector platen to inadvertently become heated and thereby activating the thermoweldable material inwardly of the perimeter of the applicator mitt. The cooling of the ejector platen beneficially limits the propensity for this undesirable welding.

Preferably, the applicator mitt tooling may be releasably engagable with the tooling actuator. The tooling actuator may be provided as a Computer Numeric Control (CNC) travelling head cutting press. The applicator mitt assembly system may also further comprise at least one mitt material feed spool for feeding mitt material to the conveyor device.

The provision of automated control functionality for the cutting and sealing of the applicator mitts ensures that uniform applicator mitts can be efficiently produced, each having a neat weld bead which is sufficiently strong and fit for purpose. This beneficially reduces the cost of manufacture of the applicator mitts. Such a travelling cutting head press may beneficially allow for more efficient material usage across the full width of mitt material, typically being of the order of 1.4 to 1.6 m.

Optionally, the mitt-perimeter cutter and weld bead may be integrally formed with one another, in which case, the mitt-perimeter cutter and weld bead may be formed from steel.

Forming the mitt-perimeter cutter and weld bead from a single piece of material limits the possibility of molten thermoweldable material from migrating into any gap between the pieces, which could delay processing of mitt material. Furthermore, whilst it may seem superficially prudent to utilise a material having very good thermal conductivity, such as copper, for the weld bead, this will limit the ability of the tooling to act as a compression cutter, and therefore steel is a more appropriate material to use.

According to a second embodiment of the invention, there is provided an applicator mitt tooling comprising: a tooling body having a mitt-perimeter cutter and weld bead thereon which are shaped to a perimeter of a mitt to be cut and welded, the mitt-perimeter cutter projecting above the weld bead in a direction away from a base of the tooling body; a heating element associated with the tooling body, the heating element being shaped so as to match a shape of the weld bead so as to create a perimeter weld for the mitt when the mitt contacts the weld bead; and an ejector platen which is actuatable relative to the tooling body to eject a cut and welded mitt away from the tooling body, the ejector platen being thermally decoupled from the tooling body.

The applicator mitt tooling could feasibly be provided in isolation, either for use with an in-part manual manufacturing process, or alternatively could be retro-fitted to existing travelling head cutting press machinery. Similarly, an easily replaceable tooling allows for ready maintenance and repair of the tooling, which could feasibly be jammed by misaligned thermoweldable material in the machinery.

The applicator mitt tooling also comprises a mitt-opening cutter, which is thermally insulated from the heating element. Additionally or alternatively, the mitt-opening cutter may be offset relative to the mitt-perimeter cutter on the applicator mitt tooling. Optionally, there may be provided a mitt-opening cutter sheath.

The mitt-perimeter cutter may be formed having a bevelled cutting edge, and may also project from the weld bead by no more than 3 mm, more preferably by no more than 1 mm, and most preferably no more than 0.5 mm.

Preferably, there may be provided a heatsink at or adjacent to the heating element. Said heatsink may be connected to the tooling body, the heating element being positioned in a recessed portion of the tooling body which is adjacent to the heatsink.

Optionally, the heating element may be elongate, in which case the heating element may be or substantially be U-shaped or tulip-shaped. The heating element may additionally or alternatively be contoured or curved to a profile of applicator mitt to be welded.

Preferably, the ejector platen may include a fluid coolant inlet and outlet to permit fluid cooling thereof. Furthermore, the ejector platen may include a plurality of sprung ejector pins to permit actuation relative to the tooling body.

According to a third embodiment of the invention, there is provided a method of assembling an applicator mitt comprising the steps of: a] feeding mitt material towards an applicator mitt assembly system, preferably in accordance with the first aspect of the invention, wherein the mitt material comprises a first layer and a second layer, one of the first and second layers having a thermoweldable layer thereon; b] actuating the applicator mitt tooling towards the conveyor device such that the mitt-perimeter cutter cuts the mitt material; c] heating a perimeter of the mitt material positioned in contact with the weld bead via the heating element so as to weld the first and second layers to one another via the thermoweldable layer; and d] ejecting the mitt material away from the tooling body using the ejector platen.

The method may further comprise the steps: e], subsequent to step d] of advancing the mitt material along the conveyor device; f] of actuating the applicator mitt tooling towards the conveyor device such that the mitt-opening cutter cuts an opening for the cut mitt material; and g] ejecting the mitt material away from the tooling body using the mitt-opening cutter sheath.

The methodology of manufacturing applicator mitts in accordance with the present invention allows for the use of welding technology to provide accurate and neat weld beads for the applicator mitts, which are strong and secure, without needing to utilise time-consuming stitching or sewing methods. This allows for a greater volume of applicator mitts to be produced, in line with the increased demand for such products.

According to a fourth embodiment of the invention, there is provided an applicator mitt comprising first and second layers, one of the first and second layers having a thermoweldable layer thereon, the first and second layers being welded to one another via heating of the thermoweldable layer at a perimeter of the first layer, preferably using a method in accordance with the third aspect of the invention.

An applicator mitt having a welded join around its perimeter does not have the visually unappealing excess material extending from its perimeter which might otherwise scratch or scrape the body of a user attempting to apply a cream or lotion. The mitt can also be formed having a visually appealing contoured perimeter, which might not otherwise be possible using traditional cutting techniques.

Preferably, the first layer may be formed from an applicator material, in which case the applicator material may be a foam material. Said thermoweldable layer may be attached an inward-facing side of the applicator material to act as a liquid-impermeable barrier to the inside of the applicator mitt. Optionally, the second layer may be formed from any one of: an applicator material; a fabric material; a plastics material; a flocked material; a velour fabric material; leatherette; and/or leather.

According to a fifth embodiment of the present invention, there is provided an applicator mitt assembly system comprising: an applicator mitt tooling including: a tooling body having a mitt-perimeter cutter and weld bead thereon which are shaped to a perimeter of a mitt to be cut; a seal formation element associated with the tooling body, the seal formation element being shaped so as to match or substantially match a shape of the weld bead so as to create a perimeter seal for the mitt when engaged with the tooling body; and an ejector platen which is actuatable relative to the tooling body to eject a cut and sealed mitt away from the tooling body, the ejector platen being thermally decoupled from the tooling body; a conveyor device adapted to feed uncut and unwelded mitt material towards the applicator mitt tooling; and a travelling head press adapted to actuate the applicator mitt tooling relative to the conveyor device to allow the mitt-perimeter cutter to cut the uncut and unwelded mitt material at the conveyor device.

Whilst an applicator mitt having a welded bead around its perimeter has been found to have sufficient strength, it will be apparent that a tooling could be provided in which the means of sealing the applicator mitt were different, and such a tooling could still be used in conjunction with a travelling head cutting press in order to achieve the efficiency of production of the earlier aspects of the invention. For example, an adhesive applicator could be used to apply a perimeter seal, or a high-frequency welding device could be used in lieu of a thermal welding apparatus.

According to a sixth embodiment of the invention, there is provided an applicator mitt assembly system comprising: an applicator mitt tooling including: a tooling body having a mitt-perimeter cutter and weld bead thereon which are shaped to a perimeter of a mitt to be cut and welded; a heating element associated with the tooling body, the heating element being shaped so as to match or substantially match a shape of the weld bead so as to create a perimeter weld for the mitt when engaged with the tooling body; and an ejector platen which is actuatable relative to the tooling body to eject a cut and welded mitt away from the tooling body, the ejector platen being thermally decoupled from the tooling body; a conveyor device adapted to feed uncut and unwelded mitt material towards the applicator mitt tooling; and a tooling actuator adapted to actuate the applicator mitt tooling relative to the conveyor device to allow the mitt-perimeter cutter to cut the uncut and unwelded mitt material at the conveyor device.

According to a seventh embodiment of the invention, there is provided an applicator mitt tooling comprising: a tooling body having a mitt-perimeter cutter and weld bead thereon which are shaped to a perimeter of a mitt to be cut; a heating element associated with the tooling body, the heating element being shaped so as to match or substantially match a shape of the weld bead so as to create a perimeter weld for the mitt when engaged with the tooling body; and an ejector platen which is actuatable relative to the tooling body to eject a cut and welded mitt away from the tooling body, the ejector platen being thermally decoupled from the tooling body.

According to an eighth embodiment of the invention, there is provided a method of assembling an applicator mitt comprising the steps of: a] feeding mitt material towards an applicator mitt assembly system, preferably in accordance with the sixth aspect of the invention, wherein the mitt material comprises a first layer and a second layer, one of the first and second layers having a thermoweldable layer thereon; b] actuating the applicator mitt tooling towards the conveyor device such that the mitt-perimeter cutter cuts the mitt material; c] heating a perimeter of the mitt material positioned at or adjacent to the mitt-perimeter cutter via the heating element so as to weld the first and second layers to one another via the thermoweldable layer; and d] ejecting the mitt material away from the tooling body using the ejector platen.

According to a ninth embodiment of the invention, there is provided an applicator mitt comprising first and second layers, one of the first and second layers having a thermoweldable layer thereon, the first and second layers being welded to one another via heating of the thermoweldable layer at a perimeter of the first layer, preferably using a method in accordance with the eighth aspect of the invention.

The invention will now be more particularly described, by way of example only, with reference to the accompanying drawings, in which:

BRIEF DESCRIPTION OF THE DRAWINGS

FIG. 3 is a magnified end perspective view of the applicator mitt tooling of FIG. 1;

FIG. 4a is a perspective representation of one embodiment of an applicator mitt tooling, in accordance with the second aspect of the invention;

FIG. 4b is a front view of the applicator mitt tooling of FIG. 4a;

FIG. 4c is a cross-section through the applicator mitt tooling at line A-A of FIG. 4b;

FIG. 4d is an exploded perspective representation of the applicator mitt tooling of FIG. 4a;

FIG. 4e is an enlarged perspective view of the mitt-perimeter cutter of the applicator mitt tooling shown in FIG. 4d;

DETAILED DESCRIPTION OF PREFERRED EMBODIMENTS

Figure 1:
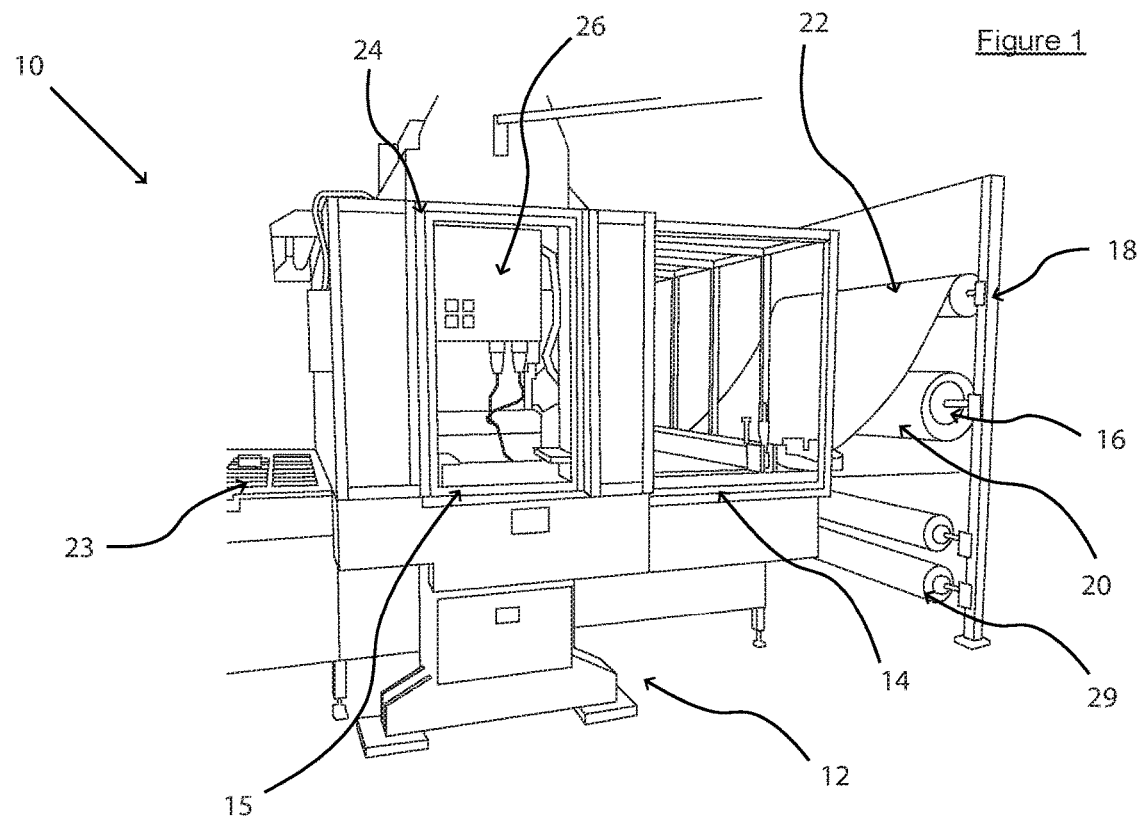
FIG. 1 is a perspective view of one embodiment of an applicator mitt assembly system, in accordance with the first aspect of the invention.
Figure 2:
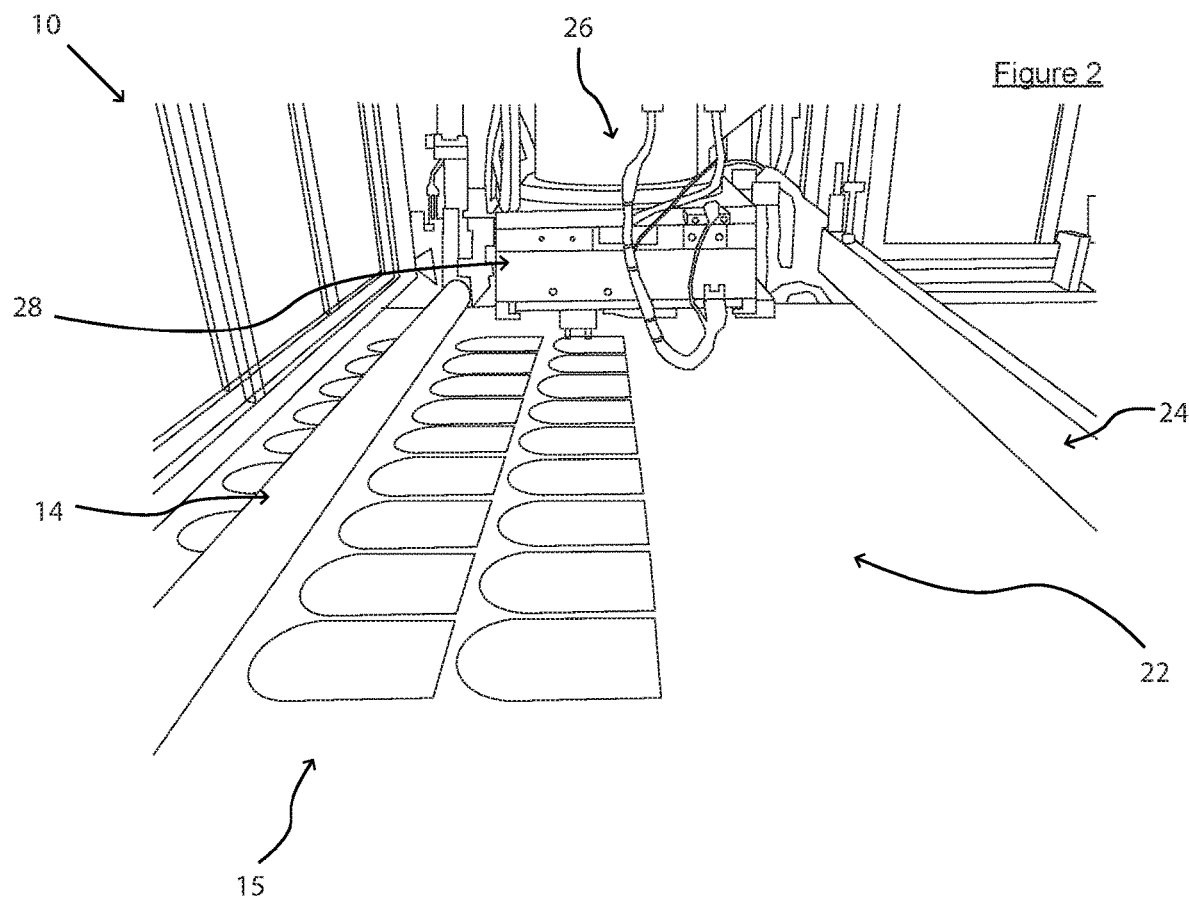
FIG. 2 is an end perspective view inside the applicator mitt assembly system of FIG. 1 showing the relative positions of the applicator mitt tooling and material used to form applicator mitts.

Referring firstly to FIGS. 1 to 3, there is shown an applicator mitt assembly system according to a preferred embodiment of the invention, indicated globally at 10, which is suitable for the production of applicator mitts, typically for the application of creams or lotions to a user.

The applicator mitt assembly system 10 includes a frame 12, chassis or similar mounting structure to which is mounted a conveyor device 14, across which the necessary materials to be formed into applicator mitts can be fed. Such a conveyor device 14 may be formed as a belt-driven machine, or similarly operable device which is capable of feeding material through towards a cutting area, such as a flexible bed or roller or more preferably a ground, hardened steel cutting bed 15, as depicted. In the depicted system 10, the conveyor device 14 is an infeed conveyor fed by first and second material spools 16, 18, which respectively provide first and second material layers 20, 22 to be formed together in the applicator mitt assembly system 10 to form an applicator mitt. A further outfeed conveyor device 23 may also be provided which is separate to the main conveyor device 14, or this could be provided with the infeed conveyor 14.

To the frame 12 is preferably mounted an enclosure 24 which here houses a CNC travelling head cutting press 26 having a specially adapted applicator mitt tooling 28 for the formation of applicator mitts. The enclosure 24 is not strictly necessary, but provides a sufficient safety barrier to protect the CNC travelling head cutting press. The CNC travelling head cutting press 26 may be mounted in place via the frame 12, be self-supporting, or may be mounted so as to depend from the ceiling of a room in which the system 10 is installed, by way of example. Whilst a CNC travelling head cutting press 26 is used in the present invention for the mass-manufacture of applicator mitts from the mitt material, it will be appreciated that any appropriate cutting press actuator arrangement could be provided in combination with the applicator mitt tooling 28 of the present invention.

As can be particularly seen in FIGS. 2 and 3, the first and second material layers 20, 22 are fed into the enclosure 24 at or adjacent to the CNC travelling head cutting press 26. A layer of cutting paper can be provided underneath the first and second material layers 20, 22 to prevent the applicator mitt tooling 28 from becoming blunted by contact with the conveyor device during the cutting process. A layer of cutting paper, seen at the lowermost spool 29 in FIG. 1, and may also be provided to limit damage to the conveyor device 14, and this can preferably be fed through with the first and second material layers 20, 22. The applicator mitt tooling 28 can then be actuated towards the first and second layers 20, 22, cutting through both layers and sealing them together. The first and second layers 20, 22 are sealed in such a manner as to form a pocket or region between the first and second layers 20, 22 into which a user of the applicator mitt will be able to insert their hand.

Once cut and sealed, the conveyor device 14 can be activated in order to extract the cut and sealed material from the enclosure 24, allowing the applicator mitts to be extracted, generally by hand to be packaged, but this process could be readily automated.

The applicator mitt tooling 28 is shown in detail in FIGS. 4a to 4e. The applicator mitt tooling 28 comprises a tooling body 30 having a mitt-perimeter cutter 32 thereon which is shaped to a perimeter of a mitt to be cut. Preferably, the tooling body 30 is integrally formed with the mitt-perimeter cutter 32, being formed from a durable material such as high-grade steel. The mitt-perimeter cutter 32 can be seen in detail in the FIG. 4e. A weld bead 34 is also be provided at or adjacent to a cutting edge 36 of the mitt-perimeter cutter 32, and this provides a solid surface which can contact with the applicator mitt material in use to form a welded join on the applicator mitt.

The weld bead 34 may be positioned inwardly of the mitt-perimeter cutter 32 so as to ensure that the welded joint of any applicator mitt formed is at or adjacent to the perimeter edge thereof. The cutting edge 36 of the mitt-perimeter cutter 32 is preferably formed so as to project above the weld bead 34 in a direction away from the base of the tooling body 30, preferably by no more than 3 mm and more preferably by no more than 1 mm, most preferably by no more than 0.5 mm, though this may be tailored depending upon the mitt material to be cut and welded. In the depicted embodiment, the mitt-perimeter cutter 32 projects 0.45 mm above the weld bead. This distance determines the pressure applied during the welding of the applicator mitt joint.

There is also provided a heating element 38 associated with the tooling body 30, the heating element 38 being shaped so as to match or substantially match a shape of the mitt-perimeter cutter 32 and weld bead 34 so as to create a perimeter weld for the mitt when engaged with and heated by the weld bead 34. Furthermore, an ejector platen 40 which is actuatable relative to the tooling body 30 is also provided so as to eject a cut and welded mitt away from the tooling body 30.

In the depicted embodiment of the applicator mitt tooling 28 is provided having a mitt-perimeter cutter 32 which has a bevelled or chamfered profile, and as such, the ejector platen 40 is provided having a complementary or substantially complementary profile so as to be receivable within an area of the tooling body 30 defined by the mitt-perimeter cutter 32.

The ejector platen 40 is actuatable relative to the tooling body 30, and in the depicted embodiment includes a plurality of ejector pins 42 mounted to a base-facing side of the ejector platen 40 which are receivable within the tooling body 38 using springs 44. This can be readily seen in the cross-sectional representation of FIG. 4c. The ejector platen 40 is preferably formed so as to be receivable within a perimeter or area defined on the tooling body 30 by the mitt-perimeter cutter 32, at or adjacent to the weld bead 34; the upstanding mitt-perimeter cutter may define a substantially enclosed region within which the ejector platen 40 is receivable.

A heatsink 46 may be provided so as to be engaged with the tooling body 30, here formed as a thermally conductive block or blocks, such as an aluminium block within which the springs 44 and ejector pins 42 are also receivable.

The heating element 38 is here formed as an arcuate and elongate strip heater, preferably having a U-shaped or tulip-shaped profile, but it will be appreciated that the shape of the heating element 38 will be largely determined by the desired shape of the applicator mitt to be formed. Here, the heating element 38 is preferably provided so as to be inserted between the tooling body 30 and heatsink 46, possibly being receivable in a shaped recess 48 in the tooling body 30. Similarly, thermocouples 50 for the heating element 38 may also be provided so as to be engagable with the body of the tooling body 30. These thermocouples 50 may be provided so as to be integrally formed with the tooling body 30, or may alternatively be releasably engagable therewith, as illustrated. Electrical connectors may be similarly provided.

The applicator mitt tooling 28 may be supported by a support plate 52 which in turn may be mounted to a distinct mounting plate 54, which can be quick-release or otherwise releasably engagable with the CNC travelling head cutting press 26. The support plate 52, which may be preferably formed from fibreboard, such as a fibreglass, may be both thermally- and compression-resistant, and protects the CNC travelling head cutting press 26 from the rigours of the welding process and may minimise thermal conduction from the heatsink 46 to the tooling 28. To facilitate quick release of the applicator mitt tooling 28, the electrical connections may be supplied to the heating element 38, for example, via a quick-release electrical connector, such as the Harting plug 56 shown.

To facilitate the extraction of cut mitt material from the applicator mitt tooling 28, the ejector platen 40 may be provided with a fluid, preferably air, cooling system, as indicated by the fluid inlet and outlets 58, 60 engaged with the ejector platen 40. This cooling permits the thermal decoupling of the ejector platen 40 from the tooling body 30, thereby preventing or limiting the likelihood of the interior portion of the applicator mitt from becoming welded during the manufacturing process. It will, however, be appreciated that the ejector platen 40 could be thermally isolated from the tooling body via other mechanisms, such as by providing a thermal insulator between the ejector platen 40 and the tooling body 30, or by forming the ejector platen 40 from a thermally insulative material. These may, however, be provided as separate insulators, such as that provided by support plate 52.

In the depicted embodiment, the mitt-perimeter cutter 32 is provided so as to only extend about a majority of the perimeter of the applicator mitt, that is, it does not cut the area in which a user would put their hand. This function may be provided by a separate mitt-opening cutter 62, preferably positioned adjacent to the arcuate portion of the mitt-perimeter cutter 32, that is, not to be correctly positioned next to the mitt-perimeter cutter 32 to cut the mitt opening of the same applicator mitt as is being cut by the mitt-perimeter cutter 32. The reasons for this will be discussed in detail below.

Here the mitt-opening cutter 62 is formed as a double-length rule blade; the depicted applicator mitt tooling 28 is a double-headed tooling, having two tooling bodies 30 to permit the cutting and sealing of two applicator mitts simultaneously. The mitt-opening cutter 62 is here designed to cut both applicator mitt openings simultaneously.

The mitt-opening cutter 62 is, in the present embodiment, thermally isolated from the heating element 38 so as to prevent accidental welding of the mitt opening during the cutting process, and this may be enhanced by the provision of the support plate 52. This is achieved by forming the support plate 52 from a thermally insulative material, but a separate dedicated insulator could be provided. Shielding 64 may also be provided between the tooling body 30 and the mitt-opening cutter 62 to limit lateral thermal interference between the two. Further cooling pipes 66 could also be provided to act as dedicated cooling for the mitt-opening cutter 62; here these pipes 66 are formed as aperture tubes to diffuse cool air around and about the mitt-opening cutter 62.

In order to prevent accidental damage of the mitt material during the sealing process, there may also be provided a mitt-opening-cutter web ejector 68 which ejects material web, that is, unused mitt material, away from the tooling body 30.

The process for forming an applicator mitt can therefore be described as follows. The first and second material layers 20, 22 of mitt material are fed together along the conveyor device towards the CNC travelling head cutting press 26, preferably above cutting paper 29. Preferably, the first material is formed from an applicator material, such as foam or sponge, and the second material is formed preferably from a fabric material, preferably a fabric material having a fine knit or yarn in order to support a strong weld. One or other of the first and second layers 20, 22 is provided having a thermoweldable layer thereon, typically but not necessarily on the applicator material, to allow for welding of the first and second layers together.

The applicator material is typically the layer having the thermoweldable material, since, due to the porous nature of the applicator material, it will generally be required to provide a barrier between the applicator material and the user's hand. Commonly, this is provided as a barrier laminate inside the applicator mitt, and such laminate may be provided so as to be thermoweldable. Additional layers may also be incorporated as part of the applicator mitt, such as textured surfaces.

It will also be appreciated that materials other than those suggested above may be provided as part of an applicator mitt, such as plastics materials. For instance, a double applicator material mitt may be provided, in which both sides of the applicator mitt are formed from the applicator material, such as foam or sponge. This allows a user to use both sides of the mitt to apply tanning solution.

Alternatively, the second layer may be formed from any one of a velour fabric material, a plastics material such as polyurethane, a flocked material, felt, leatherette, typically formed from a synthetic material, and/or leather. The user must be able to insert their hand easily into the applicator mitt, so the applicator mitt is preferable formed such that both first and second layers 20, 22 are formed from a flexible material.

Once the mitt material is in position, the CNC travelling head cutting press 26 is activated to actuate the applicator mitt tooling 28 towards the mitt material, possibly via a hydraulic actuator. As the applicator mitt tooling 28 contacts with the mitt material, the ejector platen 40 will be displaced into the tooling body 30, exposing the mitt-perimeter cutter 32. The mitt-perimeter cutter 32 can then cut through the first and second material layers 20, 22 to cut the outline of the applicator mitt, the ejector platen 40 contacting the mitt material within a region bounded by the mitt-perimeter cutter 32.

The heating element 38 is localised at or adjacent to the weld bead 34, being shaped to the perimeter of the applicator mitt. The heating element 38 may be constantly active during the manufacturing process in order to limit the effects of cooling on the tooling body 30 from slowing down the welding process. As such, simultaneously or sequentially relative to the cutting of the perimeter of the applicator mitt in the first and second layers 20, 22, the perimeter of the thermoweldable layer at the interface between the first and second layers 20, 22 is heated, with the weld bead 34 of the tooling body 30 acting as a thermocouple, resulting in the formation of a neat welded joint directly at the perimeter of the applicator mitt. The heatsink 46 can advantageously act as a thermal reservoir for the heating element 38, minimising the effects of room temperature variation on the formation of the weld bead.

The ejector platen 40, being preferably positioned within the perimeter defined by the mitt-perimeter cutter 32 provides a thermal buffer for the main body of the mitt material. Since the ejector platen is thermally decoupled from the tooling body 30, here by providing the fluid cooling system, there is minimal risk of the mitt material in contact with the ejector platen 40 from becoming welded even whilst the heating element 28 is activated.

The welded joint of the produced applicator mitt has a neat chamfered profile at the perimeter of the first, applicator material 20, rather than having any protruding or overhanging material extending around the entire perimeter of the applicator mitt. The cutting paper 29 also prevents the mitt-perimeter cutter 32 from becoming blunted upon contact with the cutting bed 15.

Once the cutting and welding of the first and second layers 20, 22 has been achieved, the CNC travelling head cutting press 26 can be retracted, allowing the ejector platen 40 to be pushed outwardly by its springs 44 and ejector pins 42. This displaces the mitt material from the heating element 38, preventing sticking of the mitt material to the applicator mitt tooling 28.

At this stage, the majority of the perimeter of the applicator mitt has been cut and sealed; however, at the position where the opening of the applicator mitt should be, the applicator mitt is still connected to the web or main bulk of the mitt material. However, since this area has not been heated, there is no danger of having welded the mitt opening shut.

The conveyor device 14 can then be further activated to feed the mitt material through the enclosure 24 by the length of one mitt. The process of cutting and sealing of the first and second layers 20, 22 can then continue. However, the mitt material which has already been cut will now be positioned beneath the mitt-opening cutter 62 of the applicator mitt tooling 28; this can be readily seen in FIGS. 2 and 3, in which the mitt material is being fed from right to left.

As the applicator mitt tooling 28 is actuated towards the mitt material, the mitt-opening-cutter web ejector 68 is displaced to reveal the mitt-opening cutter 62. This, being thermally insulated, cuts through the first and second layers 20, 22 without creating a welded joint, resulting in applicator mitts which have a neat welded joint around their main perimeter, with a neat opening into which a user can insert their hand. When the applicator mitt tooling 28 is retracted, the mitt-opening-cutter web ejector 68 pushes the uncut web away from the tooling body 30.

Figure 6:
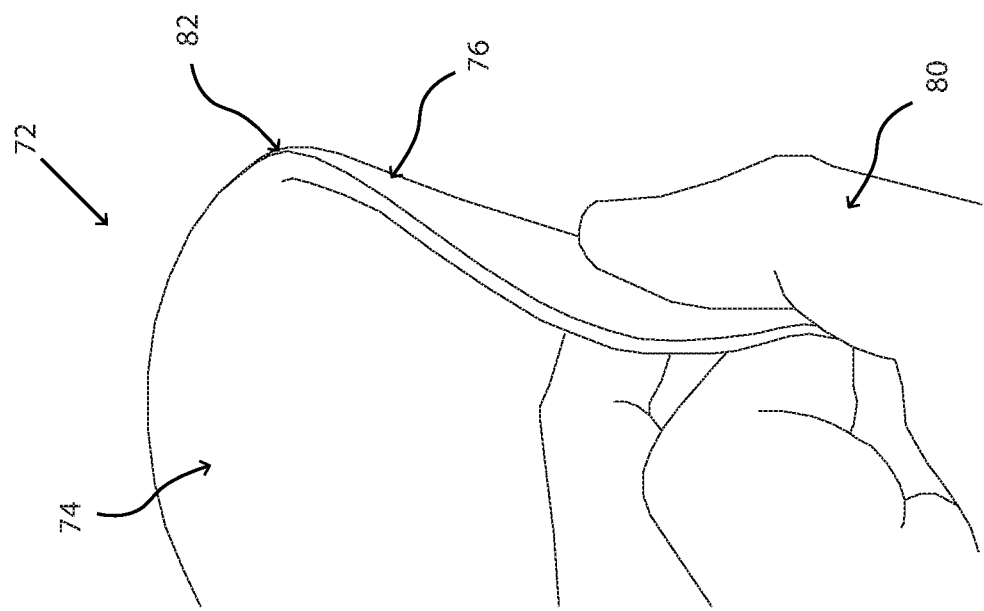
FIG. 6 shows an enlarged perspective view of an edge weld of the applicator mitt of FIG. 5.
Figure 5:
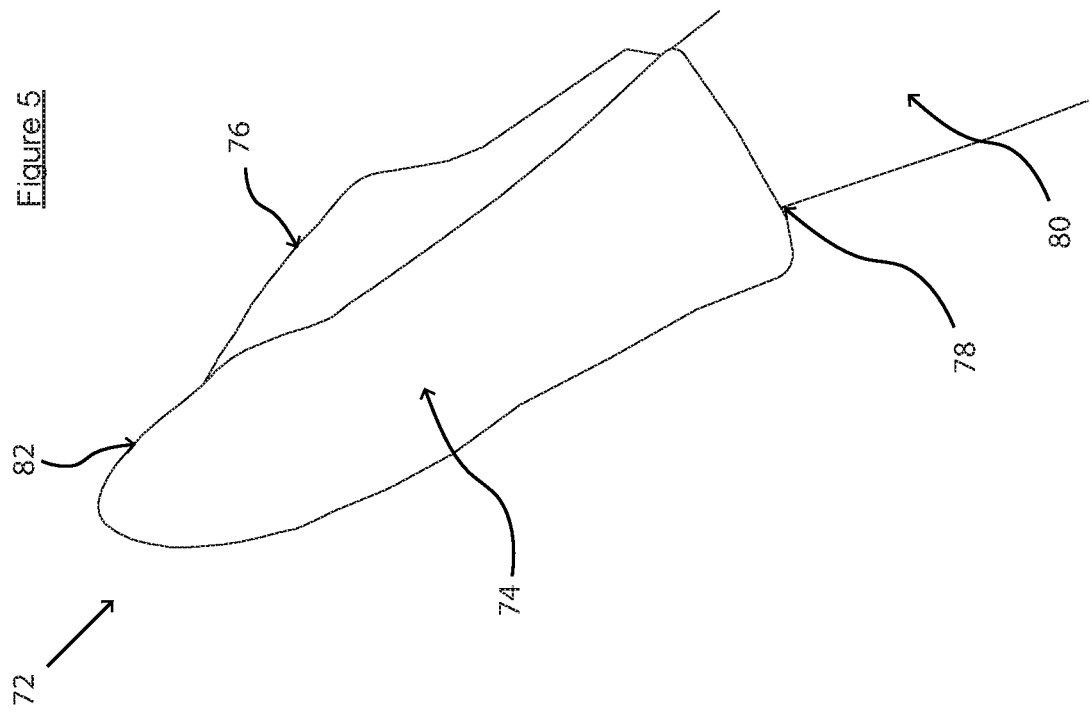
FIG. 5 is a perspective view of one embodiment of an applicator mitt formed using an applicator mitt assembly system in accordance with the first aspect of the invention.

An exemplary applicator mitt is shown in FIGS. 5 and 6, indicated globally at 72. The applicator layer 74 and fabric layer 76 are welded at their respective perimeters, with a neatly cut mitt opening 78 allowing a user 80 to insert their hand into the applicator mitt 72. Using the applicator mitt 72, the user can apply lotion or tanning solution to their body with ease.

FIG. 6 illustrates the neatness of the welded joint 82 resultant from using the applicator mitt assembly system 10 described above. There is no chaff or overhang of the fabric layer 76 which is normally associated with thermowelding flexible materials together, since there is no gap between the cutting profile of the mitt-perimeter cutter 32 and the heating element 38. The shaped mitt-perimeter cutter 32 has also allowed for a neat and contoured perimeter of the applicator mitt 72 to be produced, rather than requiring straight edges as would traditionally be the case.

Whilst a method of heating a thermoweldable layer using an applicator mitt tooling is described above, it will be clear that other methods of sealing the perimeter of an applicator mitt could also be provided in association with the requisite cutters. For instance, high-frequency welding, liquid adhesive, or fully-heated platens could alternatively be used to seal the two mitt material layers together.

A dual cutting head of the applicator mitt tooling is illustrated in the accompanying drawings; it will be apparent, however, that a single such head, or a plurality of such heads could be provided. For example, the travelling press could be rendered moot if an extended row of toolings were to be provided which spanned the width of the mitt material to be cut.

It will be apparent that whilst only a single shape of applicator mitt is shown in the accompanying drawings, that a plurality of differently shaped applicator mitts could be provided by merely altering the shape of the heating element, mitt-perimeter cutter and weld bead. In particular, the present invention could be extended so as to provide an applicator mitt having a thumbed region, and/or fingers in the applicator mitt. Symmetric applicator mitts for left and right hands could also be prepared with ease using a dual-headed applicator mitt tooling as illustrated.

Whilst the positioning of the mitt-opening cutter is such that the automation of the cutting process is achieved in a convenient manner whilst also thermally separating the mitt-opening cutter from the heating element, it is of course possible to provide the mitt-opening cutter as a discrete component of the apparatus as a whole.

It is therefore possible to provide an applicator mitt assembly system which is capable of cutting and sealing applicator mitts from mitt material in a rapid and efficient manner. The join between the layers of the applicator mitt is strong and secure, preventing accidental breakage during use of the applicator mitt, and there is no unsightly seam or join projecting from the perimeter of the applicator mitt once formed.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and not limitation. Various other modifications will be apparent to persons skilled in the art without departing from the scope of the invention—the invention being defined by the claims and equivalents thereof.

What is claimed is:

1. An applicator mitt comprising first and second layers forming first and second opposed surfaces of the applicator mitt, one of the first and second layers having a thermoweldable layer thereon, the first and second layers being attached to one another at a perimeter weld created via heating of the thermoweldable layer at a perimeter of the first layer, the perimeter weld forming a cross-sectional profile of the applicator mitt which has a bevelled or chamfered edge of the first opposed surface.

2. The applicator mitt as claimed in claim 1, wherein the first layer is formed from an applicator material.

3. The applicator mitt as claimed in claim 2, wherein the applicator material is a foam material.

4. The applicator mitt as claimed in claim 2, wherein the thermoweldable layer is attached an inward-facing side of the applicator material to act as a liquid-impermeable barrier to the inside of the applicator mitt.

5. The applicator mitt as claimed in claim 1, wherein the second layer is formed from at least one from the group consisting of: an applicator material; a fabric material; a plastics material; a flocked material; a velour fabric material; leatherette; and leather.

6. The applicator mitt as claimed in claim 5, wherein the second layer is formed from a fabric material having a fine knit or yarn to support the perimeter weld.

7. The applicator mitt as claimed in claim 1, wherein the perimeter weld creates a pocket between the first and second layers.

8. The applicator mitt as claimed in claim 1, wherein the perimeter weld extends to the edge of the applicator mitt without chaff or overhang of the first layer or the second layer.

9. The applicator mitt as claimed in claim 1, wherein the bevelled or chamfered edge profile is formed by heat deformation of the first layer.

\* \* \* \* \*